US 6,176,876 B1
(12) United States Patent
Shipkowitz et al.

(10) Patent No.: US 6,176,876 B1
(45) Date of Patent: Jan. 23, 2001

(54) LEAFLET POSITIONING FOR A MECHANICAL HEART VALVE

(75) Inventors: Tanya Shipkowitz, St. Paul; Paul J. Fordenbacher, Minneapolis; Yi-Ren Woo, Woodbury; Michael J. Girard, Lino Lakes, all of MN (US); Stephen A. Petersen, Lincoln, RI (US)

(73) Assignee: St. Jude Medical, Inc., St. Paul, MN (US)

( * ) Notice: Under 35 U.S.C. 154(b), the term of this patent shall be extended for 0 days.

(21) Appl. No.: 09/205,673

(22) Filed: Dec. 4, 1998

Related U.S. Application Data
(60) Provisional application No. 60/067,747, filed on Dec. 5, 1997.

(51) Int. Cl.$^7$ .................................................. A61F 2/24
(52) U.S. Cl. ............................................. 623/2.2; 623/2.1
(58) Field of Search .................... 623/2, 2.1, 2.2, 623/2.21, 2.22, 2.23, 2.24, 2.25, 2.26, 2.27, 2.28, 2.38, 2.39, 2.4, 2.41

(56) References Cited

U.S. PATENT DOCUMENTS

| 4,178,639 | 12/1979 | Bokros ............................ 3/1.5 |
| 4,254,508 | 3/1981 | Bokros ............................ 3/1.5 |
| 4,276,658 | 7/1981 | Hanson et al. ................... 3/1.5 |
| 4,328,592 | 5/1982 | Kalwitter ........................ 3/1.5 |
| 4,443,894 | 4/1984 | Klawitter ........................ 3/1.5 |
| 4,692,165 | 9/1987 | Bokros ............................ 623/2 |
| 5,026,391 | * 6/1991 | McQueen ....................... 623/2 |
| 5,061,278 | 10/1991 | Bicer ............................... 623/2 |
| 5,171,263 | 12/1992 | Boyer et al. ..................... 623/2 |
| 5,178,631 | 1/1993 | Waits .............................. 623/2 |
| 5,178,632 | 1/1993 | Hanson ........................... 623/2 |
| 5,192,309 | 3/1993 | Stupka et al. ................... 623/2 |
| 5,350,421 | 9/1994 | Stupka et al. ................... 623/2 |
| 5,354,330 | 10/1994 | Hanson et al. .................. 623/2 |
| 5,397,347 | 3/1995 | Cuilleron et al. ............... 623/2 |
| 5,628,792 | 5/1997 | Lentell ............................ 623/2 |
| 5,653,750 | 8/1997 | Cuilleron et al. ............... 623/2 |
| 5,741,328 | 4/1998 | Reif ................................ 623/2 |

FOREIGN PATENT DOCUMENTS

| 1053 827 | 11/1983 | (SU) . |
| WO 89/00841 | 2/1989 | (WO) . |
| WO 96/29957 | 10/1996 | (WO) . |

OTHER PUBLICATIONS

"Cineradiographic Evaluation of ATS Open Pivot Bileaflet Valves", by S. Aoyagi et al., *The Journal of Heart Valve Disease*, 1997, pp. 258–263.
Brochure entitled: "Bileaflet Mechanical Heart Valves", by St. Jude Medical, Inc. 1986.
Brochure entitled: "Mechanical Heart Valve Comparison, The St. Jude Medical®Mechanical Heart Valve and ATS Medical™Heart Valve", by St. Jude Medical, Inc., 1994.

* cited by examiner

*Primary Examiner*—David J. Isabella
*Assistant Examiner*—Alvin Stewart
(74) *Attorney, Agent, or Firm*—Hallie A. Finucane, Esq.; Westman, Champlin & Kelly, P.A.

(57) ABSTRACT

A bi-leaflet prosthetic heart valve, comprising an annular body having an upstream edge, a downstream edge and a passageway therebetween includes first and second leaflets pivotally mounted in the annular body. Each leaflet has an upstream edge, a downstream edge and a leaflet length therebetween. First and second pivot axes associated respectively with the first and second leaflets are provided and each leaflet rotates about its respective pivot axes between an open position allowing blood flow through the passageway of the annular body and a closed position blocking blood flow. The valve is configured such that the leaflets have an angle in the naturally open position of more than about 85°.

20 Claims, 11 Drawing Sheets

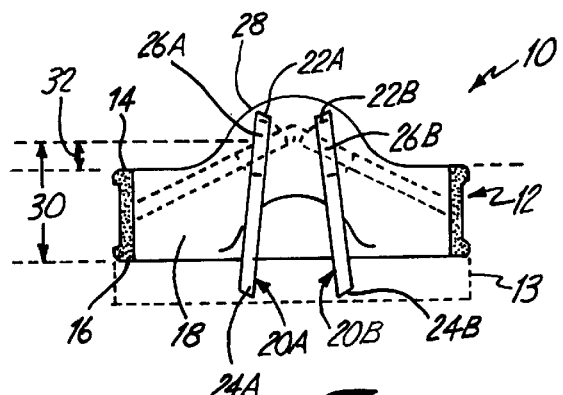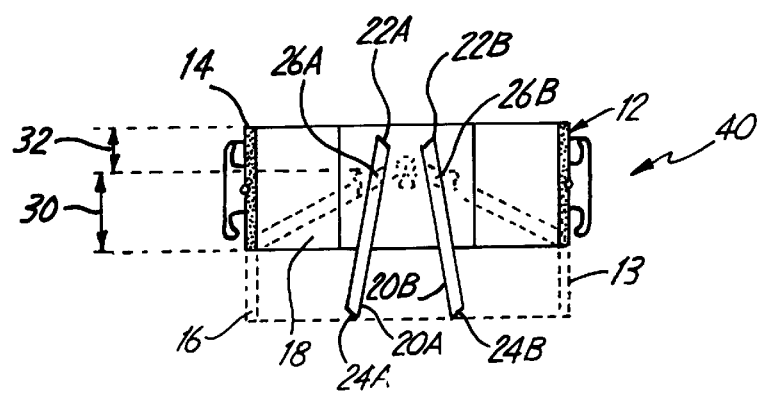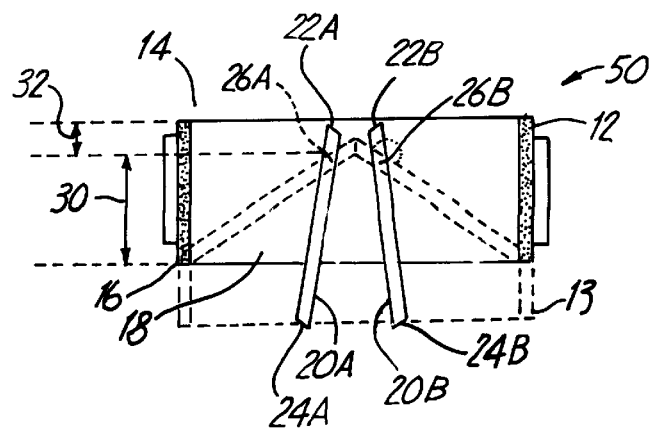

LEAFLET POSITIONING FOR A MECHANICAL HEART VALVE

The present invention claims priority to Provisional Application Ser. No. 60/067,747, filed Dec. 5, 1997, and entitled LEAFLET POSITIONING FOR A MECHANICAL HEART VALVE which is incorporated herein by reference.

FIELD OF THE INVENTION

The present invention relates to mechanical or prosthetic heart valves of the type which are used to replace the natural heart valve of a patient.

BACKGROUND OF THE INVENTION

Prosthetic heart valves are used as a replacement for natural heart valves of patients. A standard implantable mechanical heart valve typically includes an annular valve housing or body (often called an "annular body") to provide a lumen or passageway therethrough for blood flow. One or more occluders mounted to the valve are movable in response to blood flow between an open position, allowing blood flow, and a closed position, which stops or blocks blood flow in one direction. In many mechanical valves, the occluders are essentially plate-like flat or curved members called "leaflets." Typical configurations include one, two or more leaflets in the valve body.

There has been an ongoing effort to improve the efficiency of prosthetic heart valves. One critical factor in heart valve efficiency is the total area through which blood can flow when the valve is in the open position. One factor which limits the total area is how far that the leaflet(s) can open during normal operation of the valve. The more that the leaflet(s) can open to a direction that is parallel with the flow, the more efficient the valve becomes. U.S. Pat. Nos. 5,192,309 and 5,350,421 show a technique which uses a sliding pivot to increase the leaflet opening angle. However, this technique required a complex mechanism which tended to fail in actual use.

SUMMARY OF THE INVENTION

A bi-leaflet prosthetic heart valve includes an annular body having an upstream edge, a downstream edge and a passageway therebetween. First and second leaflets are pivotally mounted in the annular body and each have an upstream edge and a downstream edge. The leaflets have lengths between their upstream edge and their downstream edge. First and second leaflet pivot axes are associated respectively with the first and second leaflets and the leaflets rotate about their respective pivot axes between an open position allowing blood flow through the passageway of the valve body and a closed position blocking blood flow. The pivot axes have pivot downstream offset distances between the annular body downstream edge and the pivot axes. The leaflets have an angle in the open position of more than about 85°.

BRIEF DESCRIPTION OF THE DRAWINGS

FIG. 7 is a side cross-sectional view of a prosthetic heart valve in accordance with a design similar to a heart valve available from St. Jude Medical, Inc.

FIG. 7A is a plane view of a valve leaflet.

FIG. 8 is a side cross-sectional view of a prosthetic heart valve in accordance with a design similar to a heart valve available from CarboMedics Inc.

FIG. 9 is a side cross-sectional view of a prosthetic heart valve in accordance with a design similar to a heart valve available from ATS Medical Inc.

DETAILED DESCRIPTION OF THE PREFERRED EMBODIMENTS

Figure 1A:
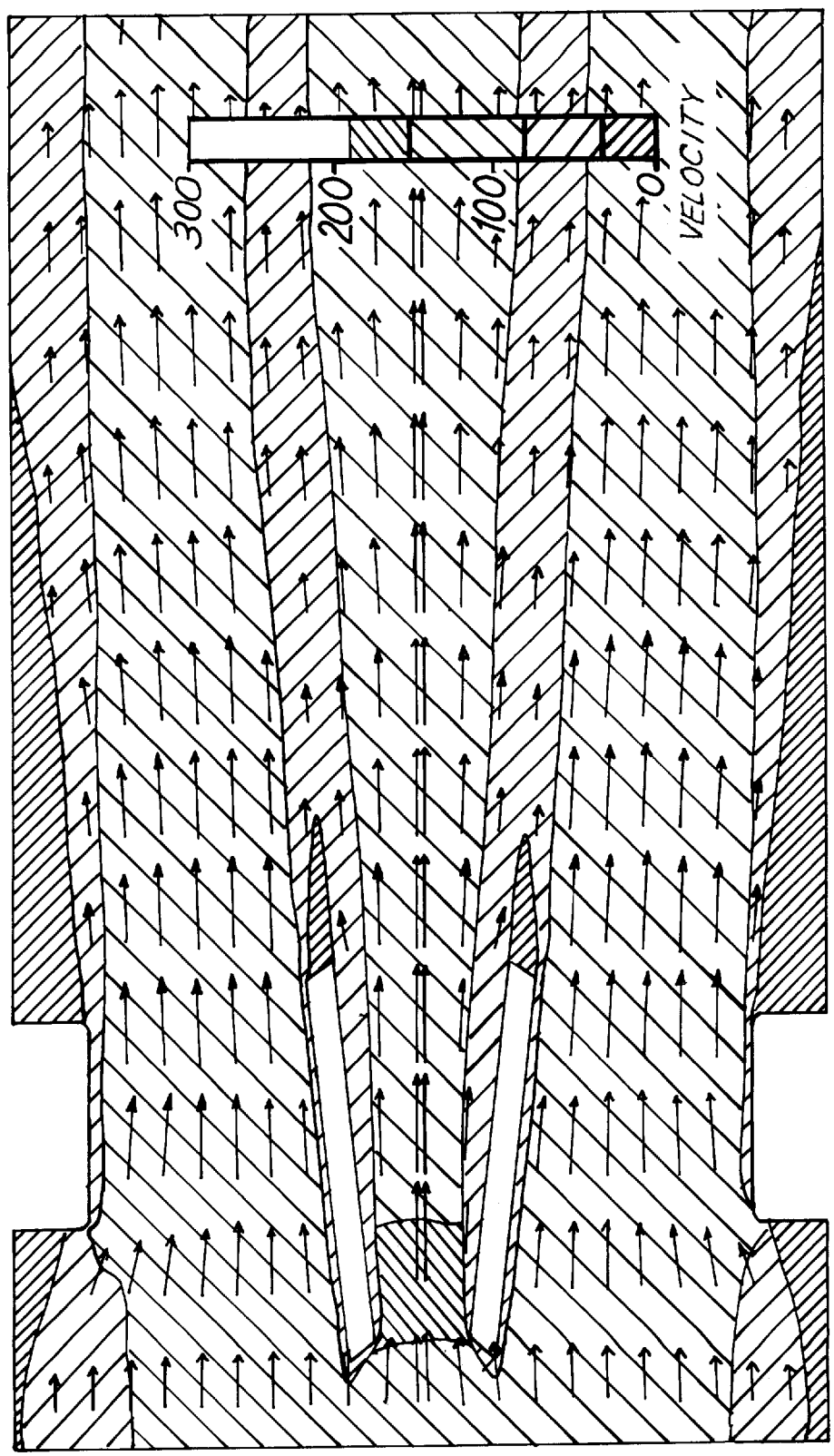
FIG. 1A is a CFD velocity vector diagram and FIG. 1B is a PIV diagram for a 25 mm St. Jude Medical, Inc. heart valve in which the leaflets are fully opened to 84°.
Figure 1B:
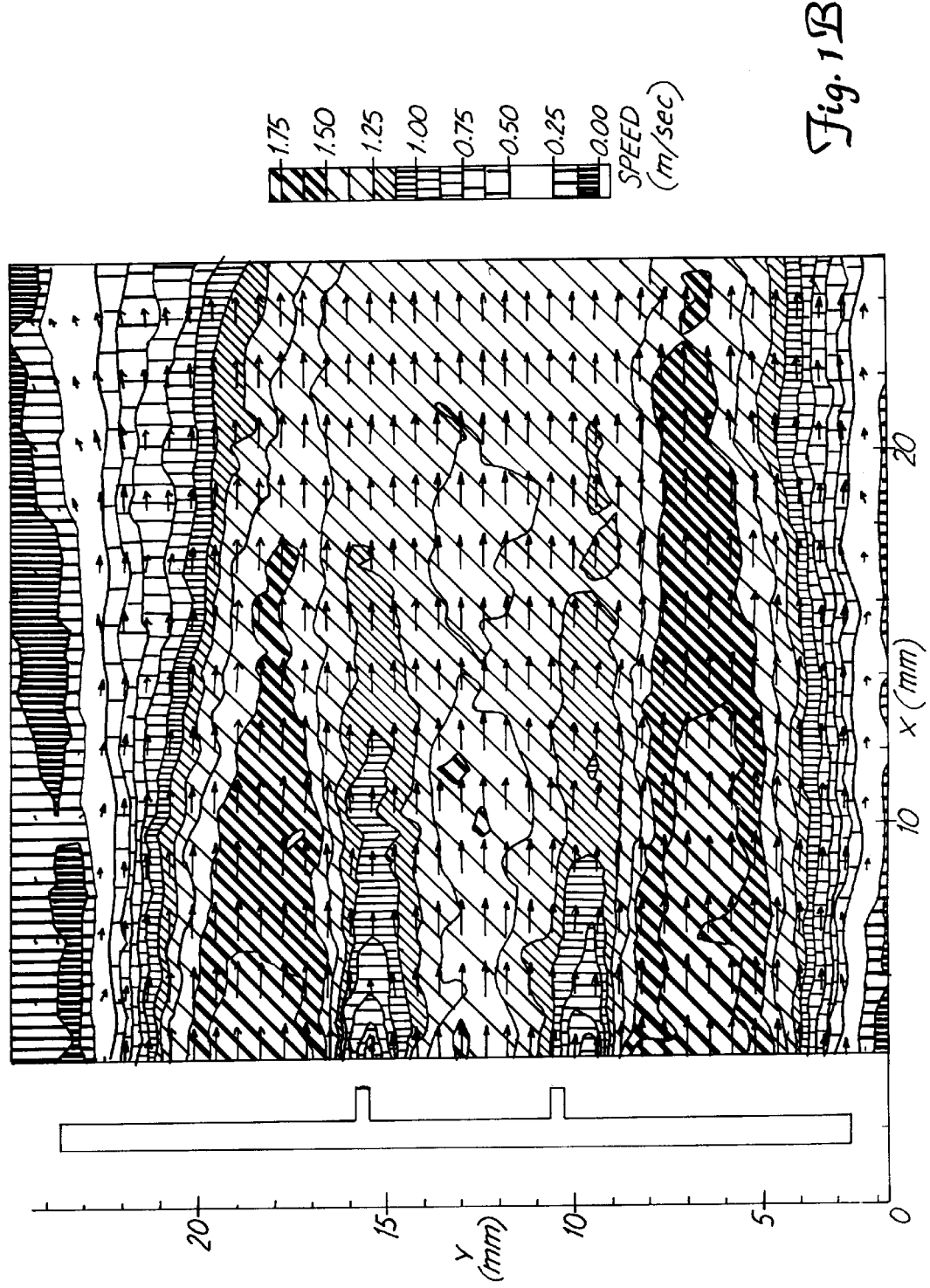
Figure 2A:
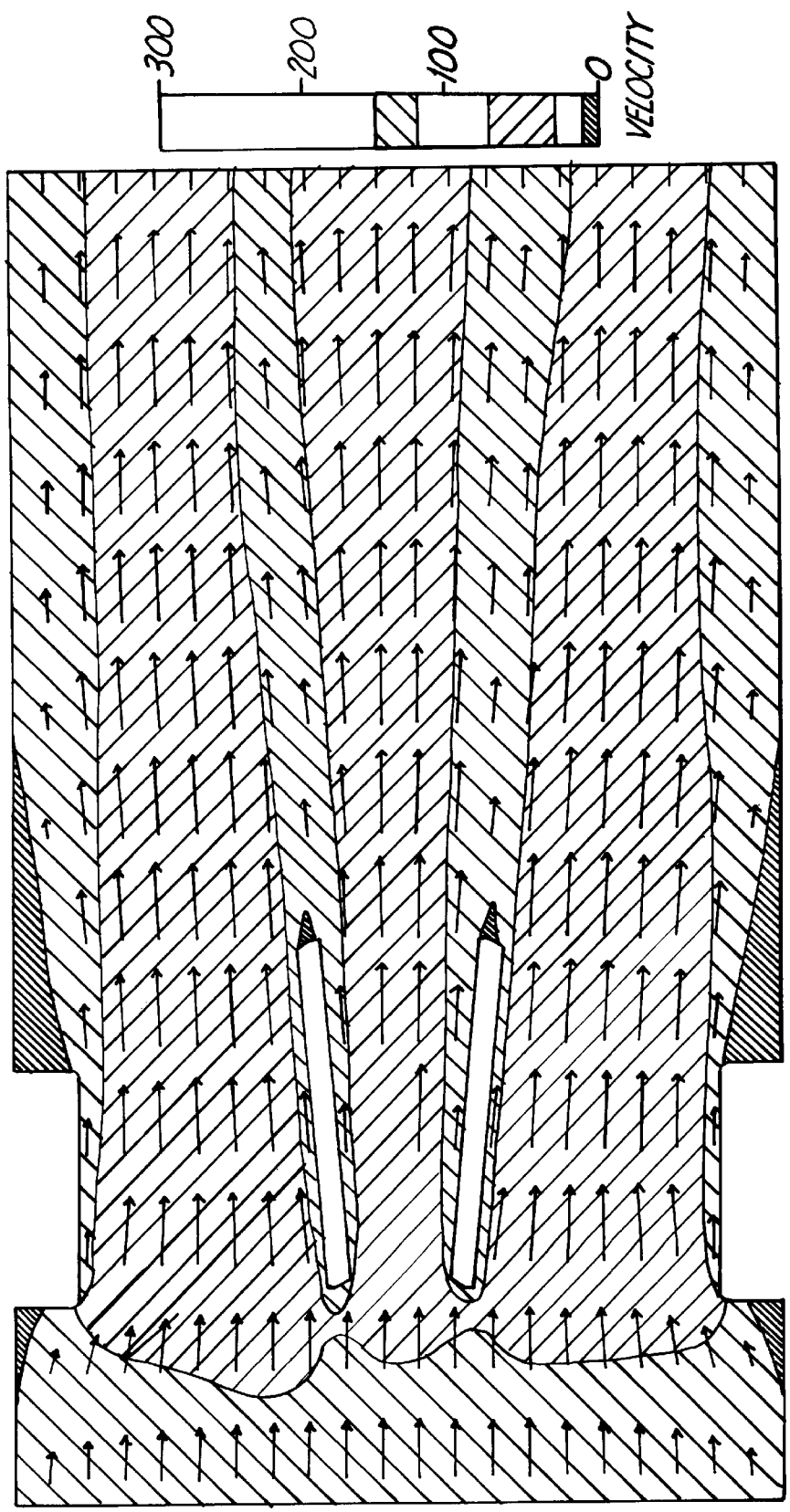
FIG. 2A is a CFD velocity vector diagram and FIG. 2B is a PIV diagram for a 25 mm ATS heart valve in which the leaflets are fixed open at 85°.
Figure 2B:
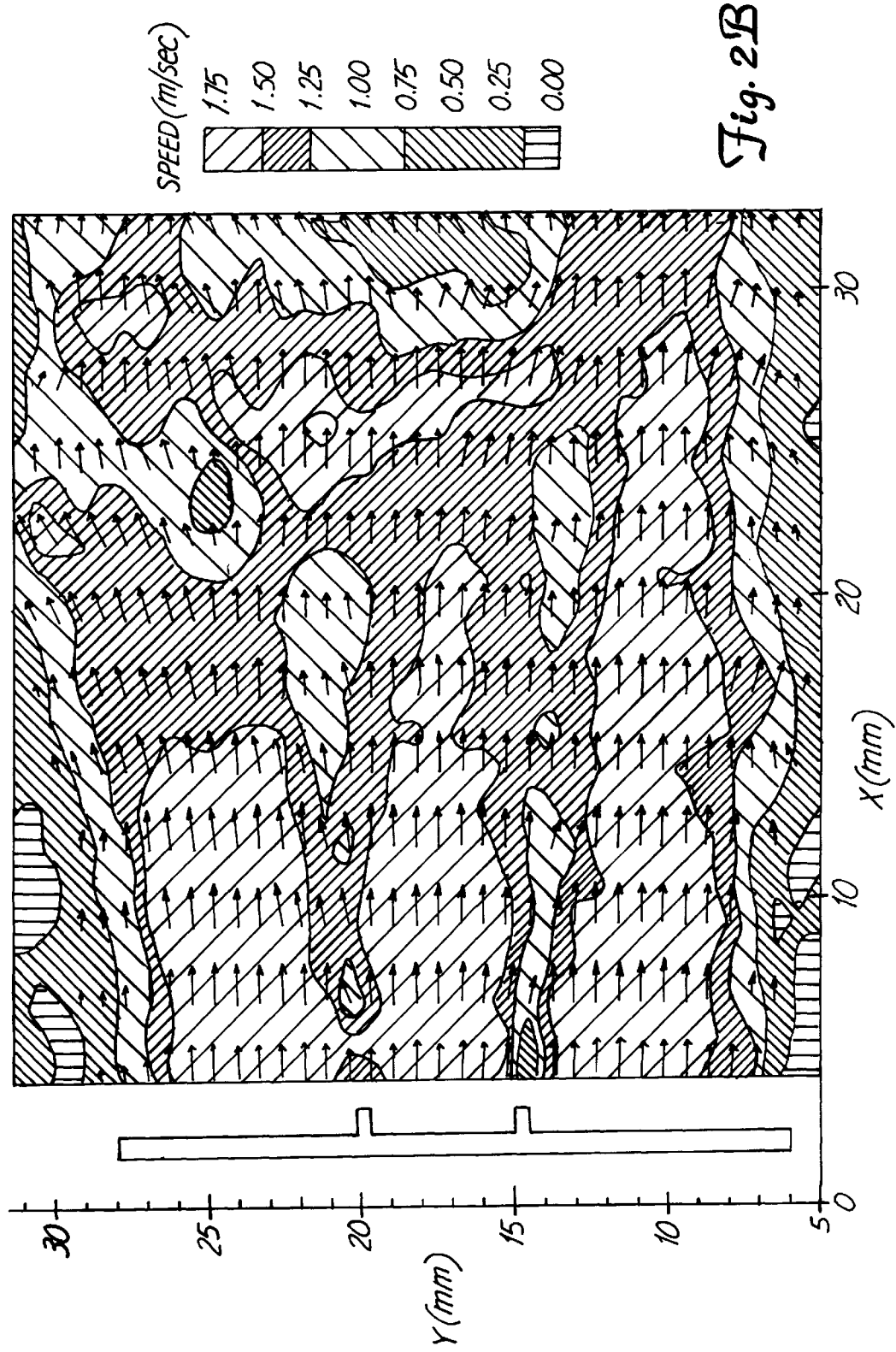

The present invention provides a bi-leaflet prosthetic heart valve in which the two leaflets are capable of opening to an angle of more than 85° relative to the plane perpendicular to the axis of the annular body. This improves the efficiency of the heart valve.

Recently, there has been clinical evidence published concerning the lack of full leaflet opening of a mechanical heart valve which was intended to open to about 85° yet only opened during normal operation to between 71° and 750. (Aoyagi et al., *J. Heart Valve Disease*, May 1997). Other valve designs have not been able to successfully attain leaflet openings equivalent to or greater than that achieved by the mechanical heart valve manufactured by St. Jude Medical, Inc. One aspect of the invention includes the recognition that leaflet opening is related to leaflet position relative to the annular body downstream edge. Leaflet opening is also influenced by leaflet position relative to the annular body upstream edge, or some combination of relative position of the leaflet to the upstream and downstream edges of the heart valve annular body.

Testing and analysis has indicated that forward blood flow converges when entering the annular body and expands upon exiting the annular body. When the leaflet downstream edge extends too far downstream from the annular body downstream edge, this affects the fluid pressure distribution across the leaflet and limits the opening angle. Computational Fluid Dynamics (CFD) results and in vitro experiments have illustrated this with various valve geometries. However, when analysis or experiments are performed with improved leaflet positions relative to the annular body by either lengthening the annular body or moving leaflets upstream, the leaflets open to a larger angle.

The St. Jude Medical® heart valve opens to 84°, the largest opening angle among all the mechanical heart valves with satisfactory clinical performance. The valve design includes a pivot guard which allows the pivots and leaflets to be positioned further upstream relative to the annular body downstream edge, without lengthening the annular body. The benefits of this design relative to leaflet opening angle have not been previously appreciated or understood in the valve industry. Consequently, the St. Jude Medical® valve does not have an optimum opening angle of 90°, where the leaflets open parallel to the blood flow.

The present invention is not limited to valves with pivot guards. The present invention provides guidelines for leaflet position as well as annular body length. The understanding of the effects of leaflet position on valve opening angle benefits all mechanical valves (i.e. mono-leaflet, bi-leaflet, or multi-leaflet, with flat or curved leaflets). The leaflet positioning and length of the annular body influence the pressure distribution across the leaflet It will also affect opening forces and wear on the pivot stops in addition to leaflet opening angle. This also applies to designs without opening pivot stops. A large leaflet opening angle is desirable to minimize pressure drop and disruption of the flow caused by leaflets at an angle to the flow.

One aspect of the invention is the recognition that leaflet positions and pivot axes location can be defined relative to the annular body downstream edge to improve valve performance. A second aspect of the invention is the recognition of the relationship between the leaflet position and pivot axes location relative to the annular body upstream edge and the leaflet opening angle. The further upstream the leaflet leading edge and the pivot axis is from the annular body upstream edge, the more favorable the fluid pressure is on the leaflet, producing a rotational moment acting to open the leaflets to a larger opening angle.

To obtain the greatest opening angle, the leading edge of the leaflet can be extended upstream of the annular body upstream edge such that the pivot axis of the leaflet is at or upstream of the annular body upstream edge and that the trailing edge of the leaflet does not extend beyond the annular body downstream edge. A series of CFD and/or in vitro analysis can be used to determine the favorable positioning of the leaflet within the annular body for a particular valve design.

CFD studies were performed to determine the moments on valve leaflets and leaflet opening angles during steady forward flow. CFD is the process of solving the mathematical equations of fluid motion on a computer to predict the flow for a given condition. In this way, flow properties were predicted based on various valve configurations and shapes to predict leaflet moments and ultimately leaflet opening angles. For a standard 25 mm St. Jude Medical® Mechanical Heart Valve® placed in a flow tube of the same size at a flow rate of 20 lpm, the resulting moment on the leaflets open to 84° was approximately 9,000 gm-cm2/s2, acting to open the leaflets. The ATS valve was also studied assuming the leaflets were open to 85°, resulting in a closing moment of 1000 gm-cm2/s2 acting to close the leaflets. From this analysis of the ATS valve, it was determined that the leaflets would not open to 85°.

A CFD study was further performed on the ATS valve with the leaflets in a 71° opening angle, the lower end of the opening range observed clinically. The resultant moment on the leaflets was 4,000 gm-cm2/s2, acting to open the leaflets. This indicated that the leaflets naturally open somewhere between 71° and 85°. Additional CFD methods were used which allow the leaflets to move under the forces of the fluid motion until equilibrium is established. The leaflets were positioned at 71° and were allowed to move to their natural position. This analysis showed that the 25 mm ATS valve leaflets open to 75°.

A CFD study was also performed on a modified ATS valve with a leaflet opening angle of 85°. This modification consisted of extending the annular body downstream edge by 2 mm in conformance with this invention. CFD analysis indicated the leaflet moment to be 700 gm-cm2/s2, acting to open the leaflets. This confirmed that the downstream extension of the leaflet past the downstream edge of the annular body plays a key role in the opening angle of the leaflets. Extending the downstream edge of the annular body by 2 mm, effectively changing the leaflet position relative to the annular body downstream edge, resulted in favorable forces which would open the leaflet to a full 85°.

In addition to CFD, Particle Image Velocity (PIV) was used to examine the steady forward flow characteristics produced with 19 mm and 25 mm St. Jude Medical® and ATS valves. Particle Image Velocity is a measurement technique which calculates instantaneous fluid velocities by tracking the displacement of particles introduced into the fluid. Velocity vector mappings can be obtained for particles projected onto a plane of light created with dual Nd:YAG lasers. The ATS valve was tested both with the leaflets artificially fixed in the fully open position (85°), as well as letting the leaflets attain their natural open position (approximately 71° to 76°). These conditions were examined to compare the flow that the design was intended to produce versus the actual valve flow performance.

Figure 3A:
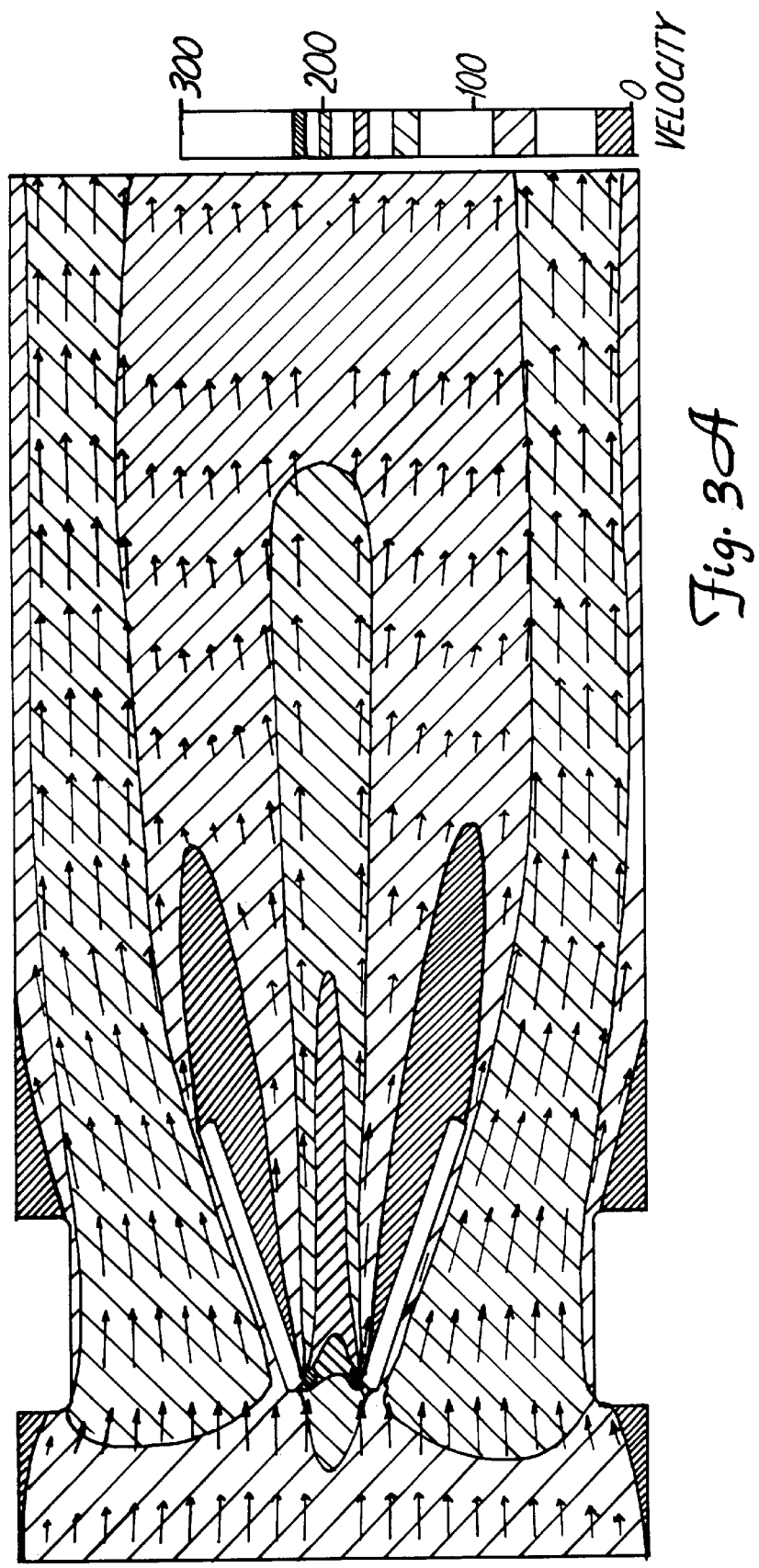
FIG. 3A is a CFD velocity vector diagram and FIG. 3B is a PIV diagram for a 25 mm ATS heart valve in which the leaflets are in their presumed natural open position of 71°.
Figure 3B:
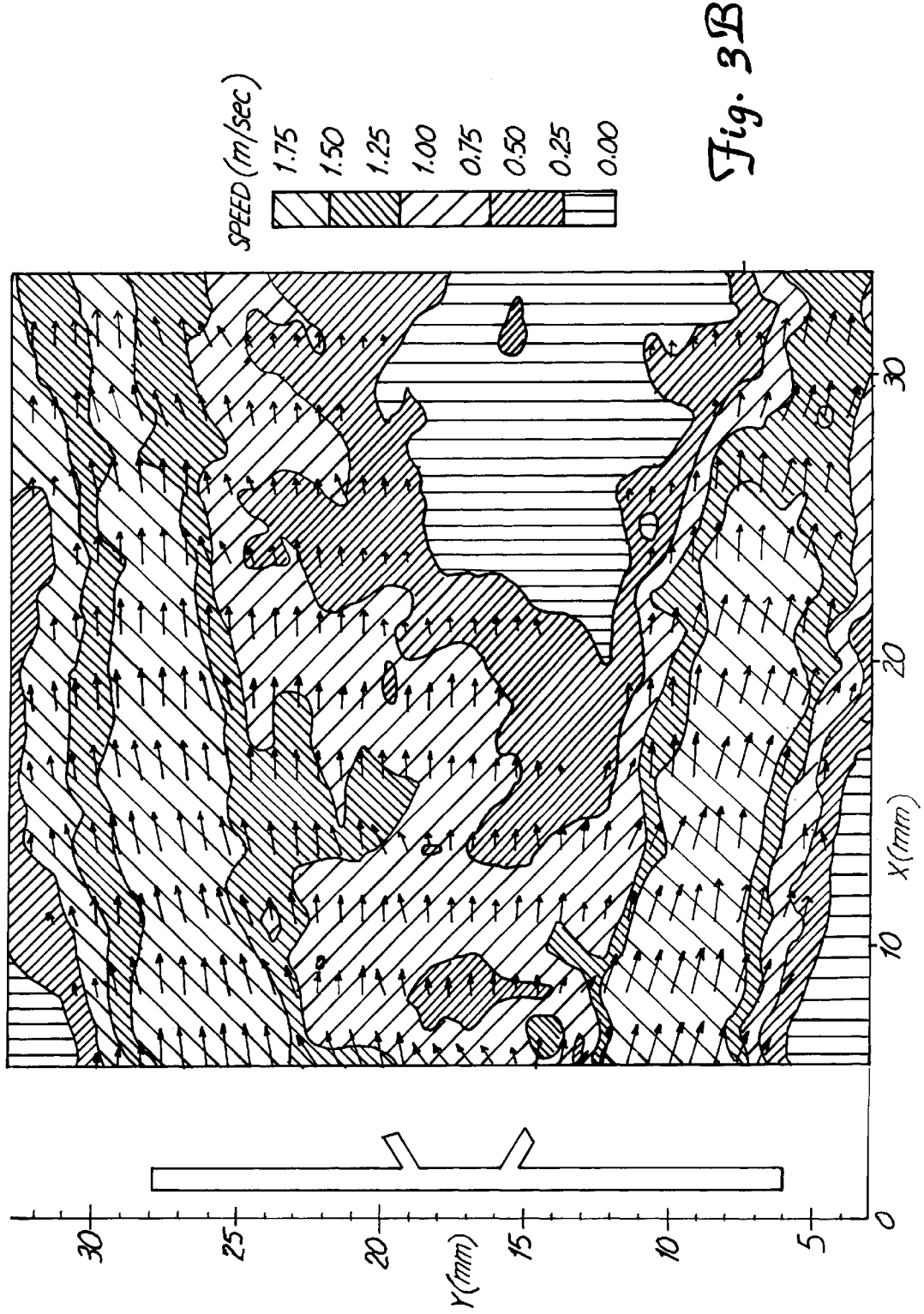

FIGS. 1A through 3B show the velocity vectors and contour plots at the valve centerline for the three geometries analyzed. The "A" figures are CFD results and the "B" figures are PIV results. A comparison of FIGS. 1A and 2A show that the SJM valve and the fully open ATS valve result in relatively undisturbed flow with small wake regions downstream of the leaflets. In contrast, the 71° open position ATS valve shown in FIG. 3A results in higher velocity jets, larger wake regions downstream of the leaflets and significant lateral flow components exiting the annular body and impinging on the downstream wall. These flow characteristics may increase thrombolytic events and decrease the efficiency of the valve. The velocity plots from the CFD analyses agree well with the experimental PIV results which are shown in FIGS. 1B, 2B and 3B. In these figures, the flow field just downstream of the valve is shown. The valve geometry was included in these figures to aid in visualization and is not drawn to scale.

Figure 4:
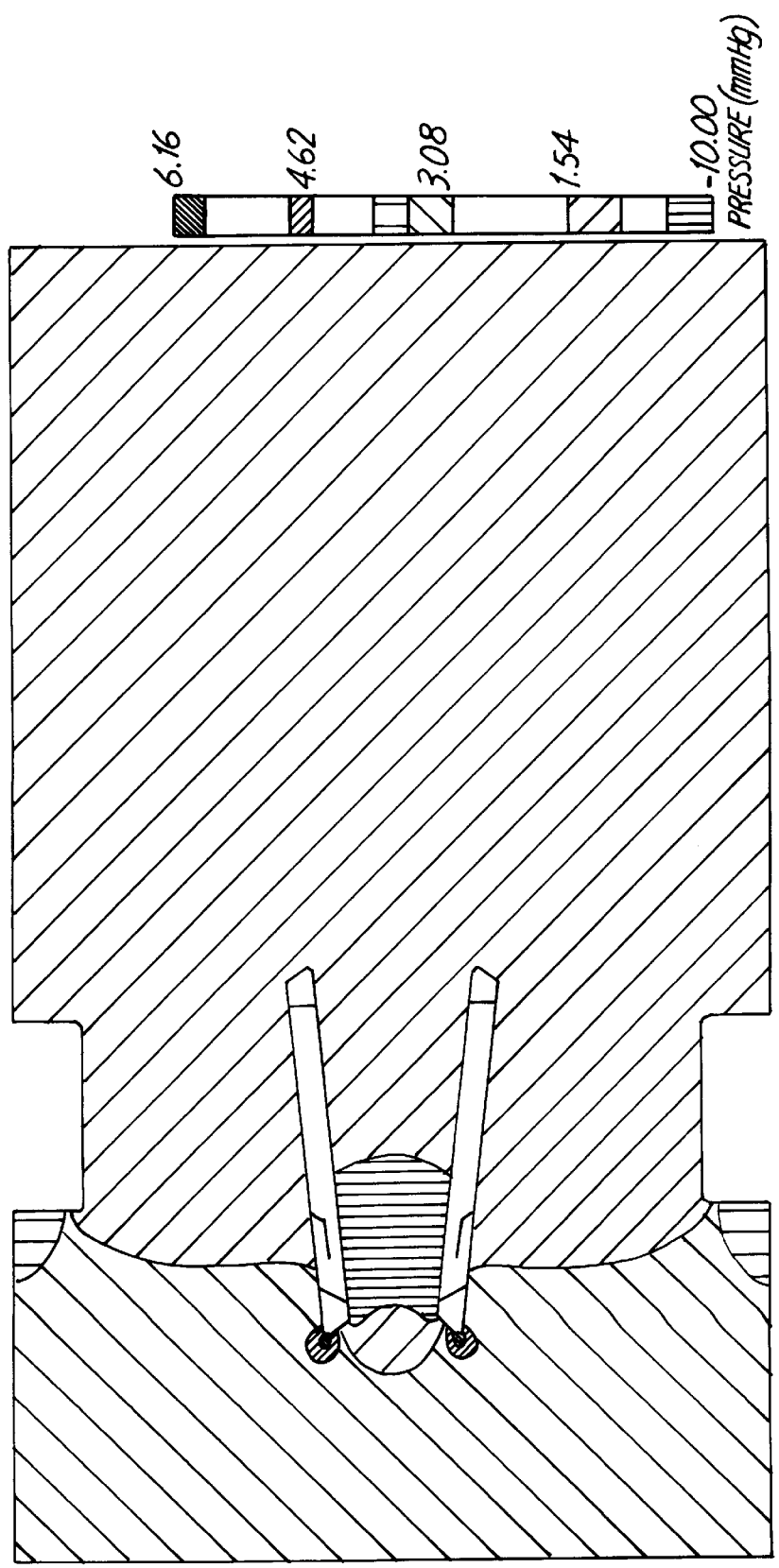
FIG. 4 is a CFD pressure contour diagram for a 25 mm St. Jude Medical, Inc. heart valve in which the leaflets are fully open to 84°.
Figure 5:
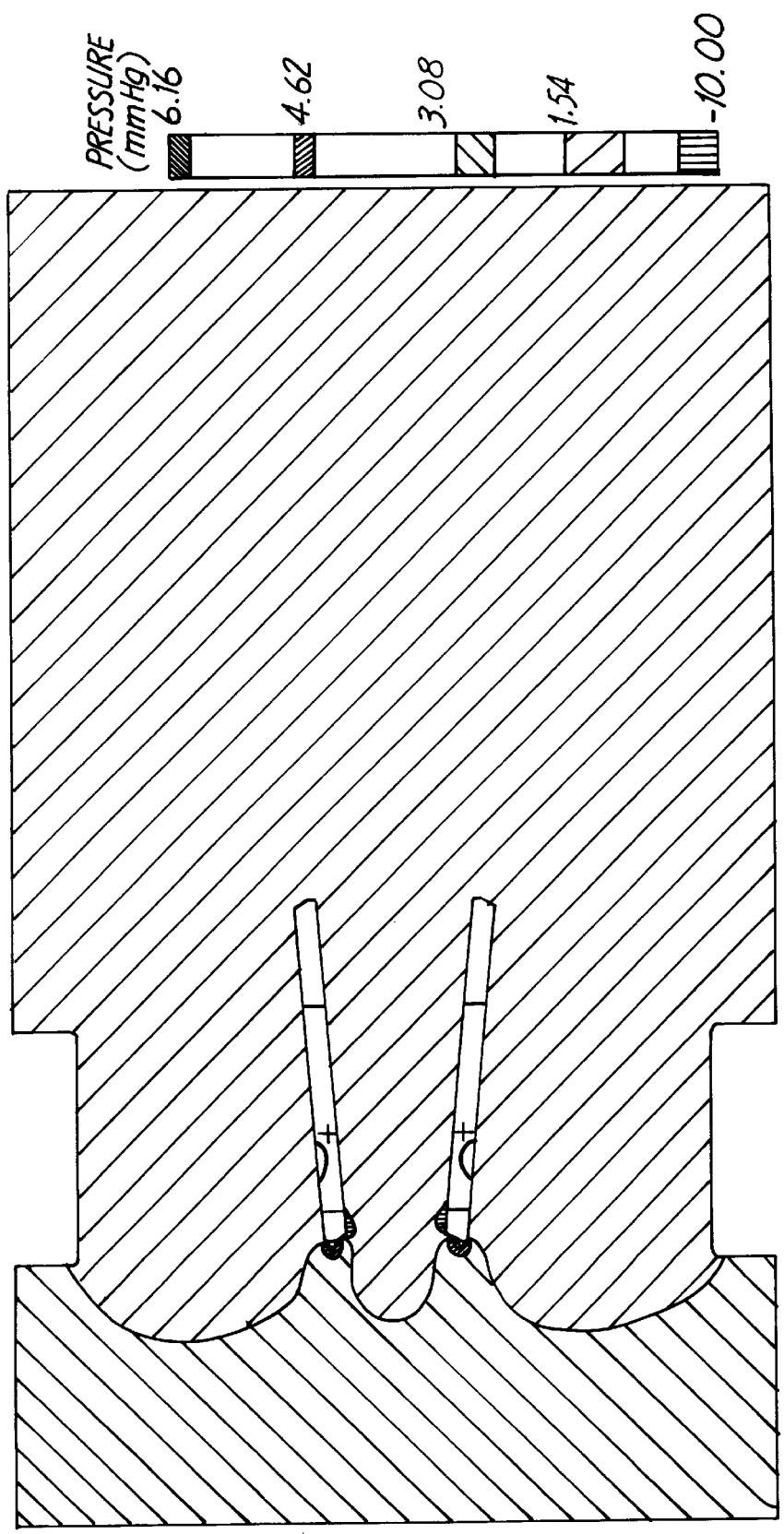
FIG. 5 is a CFD pressure contour diagram for a 25 mm ATS heart valve in which the leaflets are fixed open at 85°.
Figure 6:
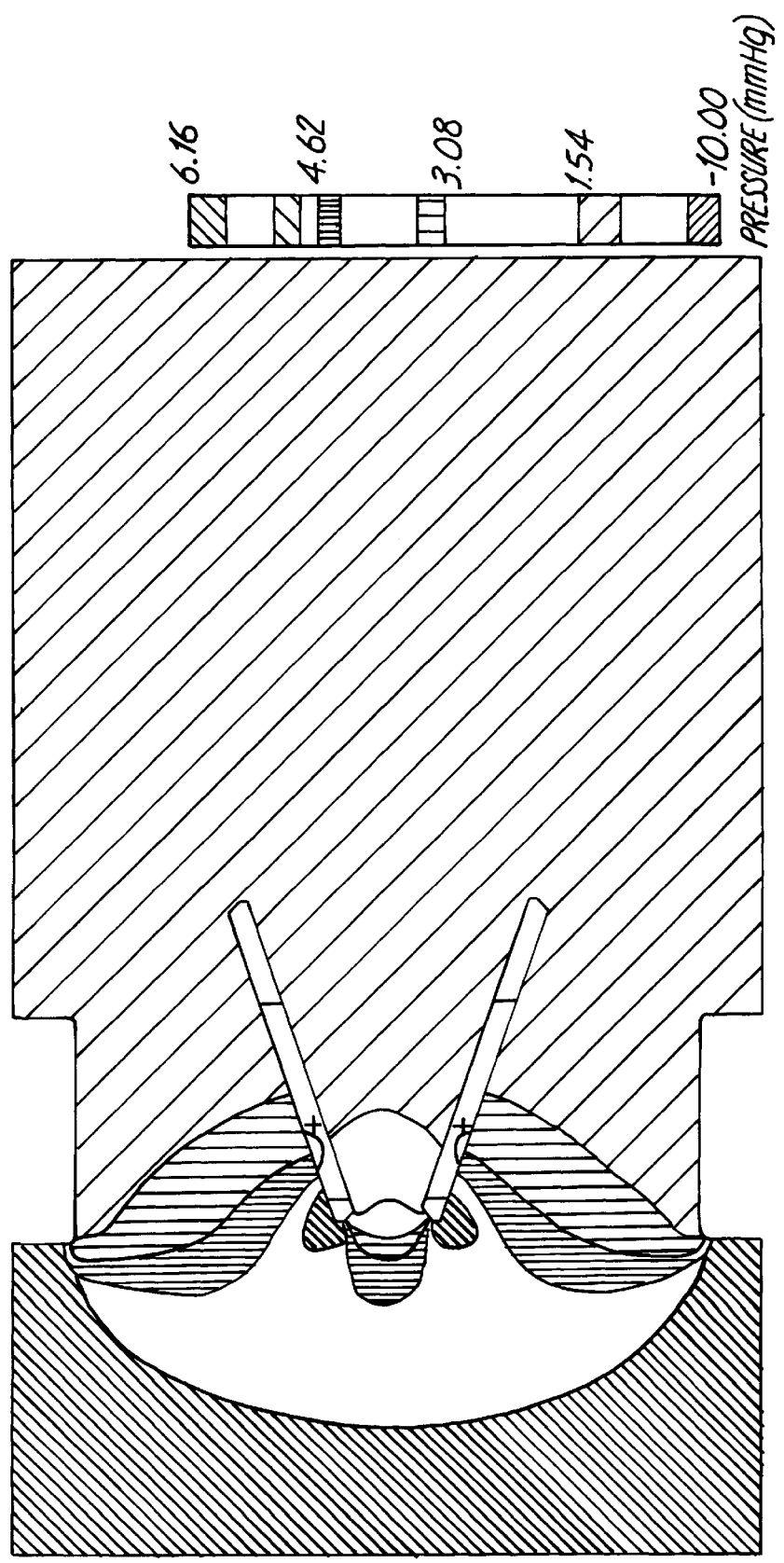
FIG. 6 is a CFD pressure contour diagram for a 25 mm ATS heart valve in which the leaflets in their presumed natural open position of 71°.

FIGS. 4, 5 and 6 show CFD contour plots of pressure at the valve centerline for the three geometries analyzed, each plotted with the same scale of maximum pressure at 6.16 mmHg. The pressure drop for the 71° position ATS is approximately double the fully open position (85°) and over 50% higher than SJM natural position (84°). This causes the heart to work harder with an ATS valve than with the SJM valve. For comparison, the CFD derived pressure gradients are 6.16, 3.94 and 3.04 mmHg for ATS 71°, SJM and ATS fully open, respectively. These results are similar to those obtained from experimental measurements. The pressure gradient comparison also confirms that a valve that has a larger leaflet opening angle has the benefit of a lower pressure gradient, resulting in a more efficient valve.

In each of the plots, the pivot locations are indicated by a cross-hair. In FIG. 5, the pressure on both sides of the fully open ATS leaflet are approximately equal downstream of the pivot location, while there is a positive net pressure difference toward the center of the valve upstream of the pivot. Thus, the net load on the leaflet produces a rotational moment about the pivot towards the closing direction. This is in agreement with experimental and clinical observations that the ATS leaflets do not open fully, since the fluid loads will not drive the leaflet to the fully open position against the stops. FIG. 6, in comparison, shows the pressures for the ATS 71° position and although there are pressures upstream of the pivot that produce a closing moment, there are counterbalancing pressures across the leaflet downstream of the pivot that produce a moment toward the open position. The resulting pressure balance acts to further open the leaflets to 75°. The SJM pressure contours in FIG. 4 indicate a larger pressure difference across the leaflet downstream of the pivot which produces a higher moment towards opening than the moment towards closing from the pressure difference upstream of the pivot. Thus, the flow induced pressure distribution keeps the SJM leaflets fully open against the opening stops.

FIGS. 7–10 show various prosthetic heart valve configurations which illustrate the present invention. FIGS. 7–10 are not drawn to scale and are provided to illustrate the locations of various distances in accordance with the invention. FIG. 7 is a side cross-sectional view of a heart valve prosthesis 10 which utilizes a design similar to the design of a heart valve available from St. Jude Medical, Inc. of St. Paul, Minn. Heart valve 10 is a bi-leaflet prosthetic heart valve and includes an annular body 12 which has an upstream edge 14 a downstream edge 16 and a passageway 18 which extends between edge 14 and edge 16. First leaflet 20A and second leaflet 20B are pivotably mounted in annular body 12 and each has an upstream edge 22A and 22B, respectively, and a downstream edge 24A and 24B, respectively. Leaflets 20A and 20B are supported by pivots and rotate about pivot axis 26A and pivot axis 26B, respectively. Leaflets 20A and 20B pivot between an open position as shown in FIG. 7 which allows blood flow through passageway 18 and a closed positioned (shown in phantom in FIG. 7) which blocks blood flow through passageway 18. In the design used in heart valve 10, pivot guards 28 extend beyond upstream edge 14 and pivot axes 26A and 26B extend therebetween.

FIG. 7 also illustrates a number of dimensions which are relevant to the present invention. A pivot downstream offset distance 30 is shown as the distance between downstream edge 16 and pivot axis 26A, 26B. Since the leaflets form a shape approximated by a half circle, the flat side being the upstream edge, and the curved edge being the downstream edge, the length from the upstream edge 22A, 22B to the downstream edge 24A, 24B of each leaflet 20A, 20B, respectively, is defined as the distance between the furthest upstream position of the leaflet upstream edge to the furthest downstream position of the leaflet downstream edge, called the leaflet length 27 and is illustrated in FIG. 7A. Further, a pivot upstream offset distance 32 is shown in FIG. 7 which is the distance pivot axis 26A, 26B is spaced above upstream edge 14, defined as the most downstream part of the upstream edge. The configuration of valve 10 also illustrates the determination of the location of the upstream edge 14 in valve configurations in which the upstream edge does not present a planer surface.

In one aspect of the invention, in a valve in which the downstream leaflet edge 24A,B is within the housing 12 when in the open position (i.e., housing 12 extends to position 13 in FIG. 7), a ratio of the pivot downstream offset distance 30 to the leaflet length 27 is more than about 0.62. Using this configuration, during normal operation of the heart valve 10, the leaflets 20A, 20B will open to an angle of more than about 85°. Preferable ranges of the ratio of the pivot downstream offset distance 30 to the leaflet length 27 include 0.62–1.0. In another aspect of the invention, in a valve in which the pivot 26A,B is set upstream from the upstream edge 14, a ratio of the pivot upstream offset distance 32 to the leaflet length 27 is more than about 0.13. In preferred embodiments of the invention, the ratio of the pivot upstream offset distance 32 to the leaflet length is 0.13 to 0.5.

FIG. 8 is a cross-sectional view of a prosthetic heart valve 40 which is similar in design to prosthetic heart valves available from CarboMedics, Inc. of Austin, Tex. FIG. 8 is useful in illustrating other aspects of the present invention. Prosthetic heart valve 40 is similar to prosthetic heart valve 10 and similar elements have been numbered the same. In the embodiment of FIG. 8, prosthetic heart valve 40 does not include pivot guards 28 (see FIG. 7) and pivot axis 26A and axis 26B are set within the valve body 12. In one embodiment, the pivot upstream offset distance 32 is between about +0.08 and about −0.15 of the leaflet length. A positive value indicates the pivot 26A,B is upstream of edge 14 and a negative value indicates a downstream location as illustrated in FIG. 8. In such an embodiment, the ratio of the pivot downstream offset distance 30 to the leaflet length should be between about 0.44 and about 0.62. In yet another embodiment of the invention, this ratio is greater than about 0.44.

These guidelines are applicable to other valve configurations. For example, FIG. 9 is a cross-sectional view of a prosthetic heart valve 50 which is similar in design to prosthetic heart valves available from ATS Medical Inc. of St. Paul, Minn. Valve 50 is similar to valve 40 and similar elements are numbered the same. The various ratios described above can be applied to valve 50 to achieve a leaflet natural open position of more than 85°. For all valves having leaflet opening stops, the stops will need to be modified or eliminated to allow the leaflets to achieve a greater than 85° opening angle.

Figure 10:
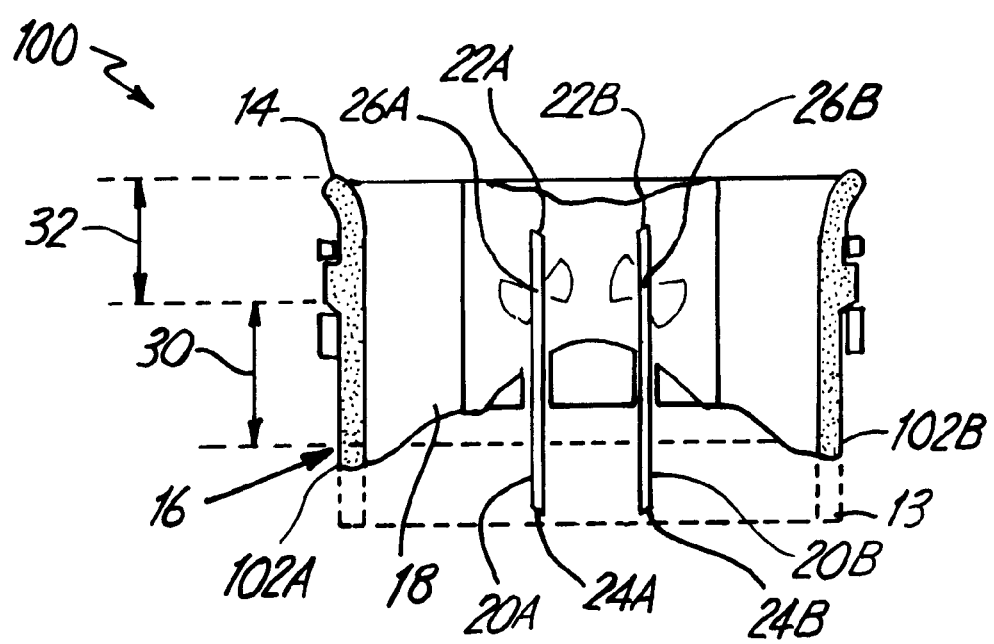
FIG. 10 is a side cross-sectional view of a prosthetic heart valve in accordance with a design similar to a heart valve available from Medical Carbon Research Institute.

FIG. 10 is a side cross-sectional view of a prosthetic heart valve 100 which has a design similar to the On-X valve from Medical Carbon Research Institute of Austin, Tex. Heart valve 100 is similar in design to heart valves 40 and 50 shown in FIGS. 8 and 9, respectively, except heart valve 100 includes trailing edge extensions 102A and 102B. Elements in heart valve 100 which are similar to elements in heart valves 40 or 50 are numbered the same. The configuration of valve 100 also illustrates the determination of the location of the downstream edge 16 in valve configurations in which the downstream edge does not present a planar surface. As used herein, the annular body downstream edge is defined as a plane perpendicular to the annular body axis which contains the average value of the downstream edge location. The average value can be determined using a simple integration:

$$\frac{\int x ds}{\int ds}$$

where x is the shortest distance from the pivot axis to the annular body downstream edge along the axis of the annular body and ds is the differential length of the annular body downstream edge projected onto a plane which is perpendicular to the center axis of the annular body. The integration is carried out along the perimeter of the annular body downstream edge.

The present invention provides design criteria that can increase the opening angle of a prosthetic heart valve to more than about 85°. This allows the leaflets to be nearly parallel to the blood flow which improves valve efficiency. This design criteria may be used on valve designs having or not having leaflet opening stops. In one aspect, the relationship between the position of the pivots relative to the annular body and leaflet opening relies exclusively on the pivoting action without sliding motion of the leaflet.

In another aspect of the invention pivots 26A, 26B do not include pivot stops. In such a design, the leaflets 20A, 20B open naturally to a desired angle and close to a point where the leaflets 20A, 20B touch the valve body 12 or each other. The flow through the pivot will be unhindered by pivot stops, lessening flow disruption and increasing valve efficiency. Since the pivot does not need opening stops there will be no impact or frictional wear/damage associated with the leaflet "ear" impacting or rubbing against the pivot opening stops. This will also facilitate the use of coatings in this area. These coatings may be of the type to resist or prevent blood coagulation or thrombus formation. Since the contact of the leaflet against the pivot surface will be minimized, the coating wear (due to abrasion) will be minimized.

Although the present invention has been described with reference to preferred embodiments, workers skilled in the art will recognize that changes may be made in form and detail without departing from the spirit and scope of the invention. Those skilled in the art will recognize that the invention may be applied to any type of valve design including the Edwards-Duromedics from Baxter of California and the Bicarbon valve from Sorin Biomedica of Italy in which the leaflets have a curved design.

What is claimed is:

1. A bi-leaflet prosthetic heart valve, comprising:
    an annular valve body having an upstream edge, a downstream edge and a passageway therebetween;
    first and second leaflets pivotally mounted in the valve body, each leaflet having an upstream edge, a downstream edge and a leaflet length therebetween, the leaflets having substantially planar upstream and downstream surfaces;
    first and second pivot axes associated respectively with the first and second leaflets, wherein each leaflet rotates about its respective pivot axes between an open position allowing blood flow through the passageway of the valve body and a closed position blocking blood flow, the pivot axes having pivot upstream offset distances between the upstream edge and the pivot axes; and
    wherein a ratio of the pivot upstream offset distance to the leaflet length is more than about 0.13, whereby during operation of the heart valve, the leaflets have an angle in the open position of more than about 85°.

2. The bi-leaflet prosthetic heart valve of claim 1 including open stops to limit the open position of the valve.

3. The bi-leaflet prosthetic heart valve of claim 1 wherein the pivot has a pivot downstream offset distance and a ratio of the pivot downstream offset distance to the leaflet length is more than about 0.62.

4. The bi-leaflet prosthetic heart valve of claim 3 wherein the ratio of the pivot downstream offset distance to the leaflet length is less than about 1.

5. The bi-leaflet prosthetic heart valve of claim 1 wherein the pivot has a pivot upstream offset distance and a ratio of the pivot upstream offset distance to the leaflet length is less than about 0.5.

6. The bi-leaflet prosthetic heart valve of claim 1 including pivot guards which extend upstream of the upstream edge and wherein the pivots are positioned in the pivot guards.

7. The bi-leaflet prosthetic heart valve of claim 1 wherein the pivots comprise protrusions.

8. The bi-leaflet prosthetic heart valve of claim 7 wherein depressions formed in the valve body are adapted to receive the protrusions.

9. The bi-leaflet prosthetic heart valve of claim 1 wherein the annular body downstream edge has a curved profile.

10. A bi-leaflet prosthetic heart valve, comprising:
    an annular valve body having an upstream edge, a downstream edge and a passageway therebetween;
    first and second leaflets pivotally mounted in the valve body, each leaflet having an upstream edge, a downstream edge and a leaflet length therebetween;
    first and second pivot axes associated respectively with the first and second leaflets, wherein each leaflet rotates about its respective pivot axes between an open position allowing blood flow through the passageway of the valve body and a closed position blocking blood flow, the pivot axes having pivot downstream offset distances between the downstream edge and the pivot axes, the pivot axes positioned downstream of the upstream edge; and
    wherein a ratio of the pivot downstream offset distance to the leaflet length is more than about 0.62, whereby during operation of the heart valve, the leaflets have an angle in the open position of more than about 85°.

11. The bi-leaflet prosthetic heart valve of claim 10 including open stops to limit the open position of the valve.

12. The bi-leaflet prosthetic heart valve of claim 10 wherein the pivots comprise protrusions.

13. The bi-leaflet prosthetic heart valve of claim 12 wherein the depressions are formed in the valve body.

14. The bi-leaflet prosthetic heart valve of claim 10 wherein the annular body downstream edge has a curved profile.

15. A bi-leaflet prosthetic heart valve, comprising:
    an annular valve body having an upstream edge, a downstream edge and a passageway therebetween;
    first and second leaflets pivotally mounted in the valve body, each leaflet having an upstream edge, a downstream edge and a leaflet length therebetween, the leaflets having substantially planar upstream and downstream surfaces;
    first and second pivot axes associated respectively with the first and second leaflets, wherein each leaflet rotates about its respective pivot axes between an open position allowing blood flow through the passageway of the valve body and a closed position blocking blood flow, the pivot axes having pivot downstream offset distances between the downstream edge and the pivot axes, the pivot axes having an upstream offset distance of between about −0.15 and about 0.08 of the leaflet length; and
    wherein a ratio of the pivot downstream offset distance to the leaflet length is between about 0.44 and about 0.62, whereby during operation of the heart valve, the leaflets have an angle in the open position of more than about 85°.

16. The bi-leaflet prosthetic heart valve of claim 15 including open stops to limit the open position of the valve.

17. The bi-leaflet prosthetic heart valve of claim 15 wherein the pivots comprise protrusions.

18. The bi-leaflet prosthetic heart valve of claim 17 wherein the depressions are formed in the valve body.

19. The bi-leaflet prosthetic heart valve of claim 15 wherein the annular body downstream edge has a curved file.

20. The bileaflet prosthetic heart valve of claim 10 wherein the first and second leaflets have substantially planar upstream and downstream surfaces.

* * * * *

UNITED STATES PATENT AND TRADEMARK OFFICE
CERTIFICATE OF CORRECTION

PATENT NO. : 6,176,876 B1
DATED : January 23, 2001
INVENTOR(S) : Tanya Shipkowitz et al.

It is certified that error appears in the above-identified patent and that said Letters Patent is hereby corrected as shown below:

<u>Column 8,</u>
Line 62, change "file" to -- profile --.

Signed and Sealed this

Twenty-ninth Day of January, 2002

Attest:

*Attesting Officer*

JAMES E. ROGAN
*Director of the United States Patent and Trademark Office*